United States Patent [19]

Dietrick et al.

[11] Patent Number: 4,932,842
[45] Date of Patent: Jun. 12, 1990

[54] SUCTION GENERATOR

[75] Inventors: Gerald P. Dietrick; Michael J. Vagedes, both of Florence, Ky.

[73] Assignee: Vagedes Industries, Inc., Elsmere, Ky.

[21] Appl. No.: 335,715

[22] Filed: Apr. 10, 1989

[51] Int. Cl.⁵ .............................................. B01D 47/06
[52] U.S. Cl. ...................................... 417/169; 55/228; 239/524
[58] Field of Search ............... 417/151, 169, 174, 179; 239/524; 261/78 A, 78.1; 55/228

[56] References Cited

U.S. PATENT DOCUMENTS

| | | | |
|---|---|---|---|
| 2,358,690 | 11/1942 | Decker | 417/179 |
| 2,892,582 | 6/1959 | O'Rourke | 417/179 |
| 3,618,772 | 11/1971 | Dietrick | 210/104 |
| 3,707,067 | 12/1972 | Dietrick | 55/228 |
| 4,880,357 | 11/1989 | Mathers | 417/77 |

FOREIGN PATENT DOCUMENTS

| | | | |
|---|---|---|---|
| 0297550 | 1/1989 | European Pat. Off. | 417/169 |
| 004900 | 1/1986 | Japan | 417/169 |

Primary Examiner—Leonard E. Smith
Assistant Examiner—Robert N. Blackmon
Attorney, Agent, or Firm—Wood, Herron & Evans

[57] ABSTRACT

A suction apparatus useful as a vacuum pump, aerator or the like comprises a fluid inlet housing having a nozzle support plate which includes a plurality of nozzles having a discharge outlet located within a suction chamber. These nozzles each align with the passageway of a hollow suction tube having an inlet within the suction chamber and an outlet spaced from a deflector plate. A fluid such as liquid is ejected from the discharge outlet of the nozzles and in the course of passage into the suction tubes a negative pressure is created within the suction chamber which draws a second fluid such as air through the suction chamber and into the passageway of the suction tubes for combination with the liquid therein forming a combined liquid-gas fluid stream. This combined fluid stream is ejected from the outlet of the suction tubes and impacts the deflector plate which creates a back pressure causing the combined fluid stream to enlarge or expand within the suction tubes and form a liquid seal therein which substantially prevents the leakage of air from the outlet of the suction tubes into the suction chamber.

17 Claims, 2 Drawing Sheets

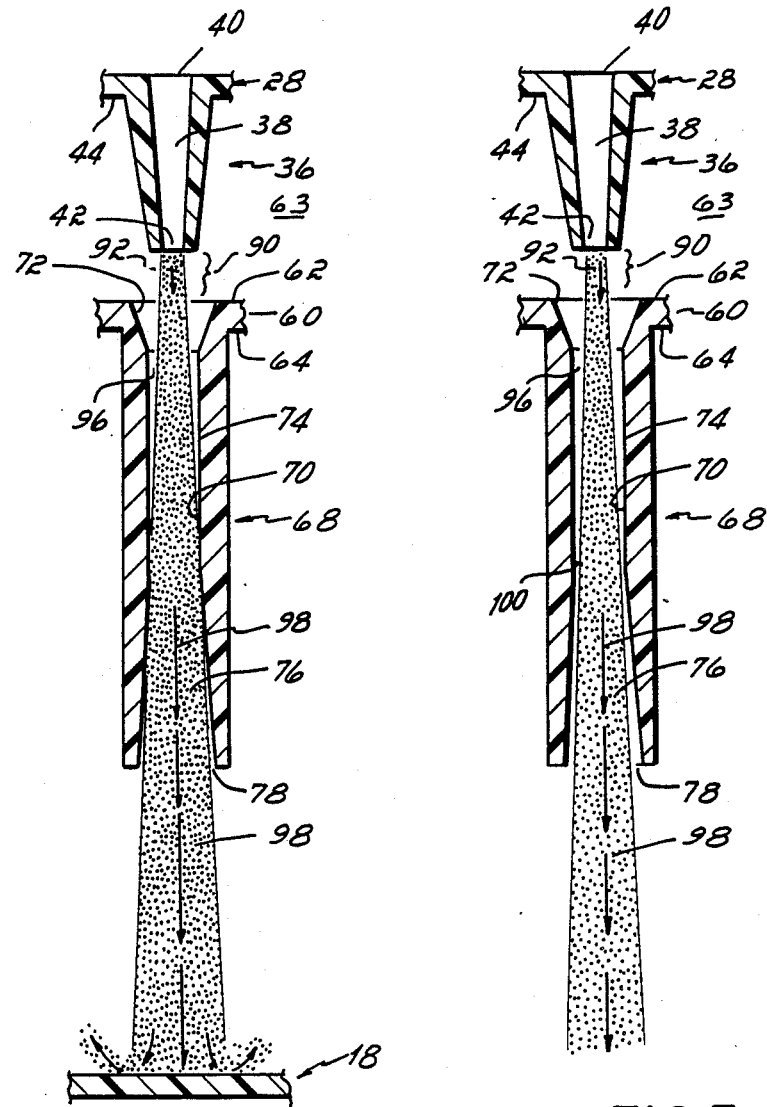

SUCTION GENERATOR

FIELD OF THE INVENTION

This invention relates to suction apparatus, and, more particularly, to a suction generator useful as a vacuum pump, an aerator and the like.

BACKGROUND OF THE INVENTION

Apparatus have been employed in the prior art in which a liquid is directed under pressure into one or more nozzles and ejected in a stream from the discharge outlet of each nozzle directly into the inlet of a hollow tube which is spaced from the nozzle. The discharge outlet of the nozzles and the inlets of the hollow tubes are located within a suction chamber connected to a source of fluid, e.g., air, to be pumped. In the course of passage between the discharge outlet of the nozzles and the inlets of the hollow tubes, the liquid streams ejected from the nozzles create a negative pressure within the suction chamber which draws the air through the suction chamber and into the hollow tubes. The air is intermixed with the liquid stream within the hollow tubes forming a combined fluid stream which is ejected from the outlet end of the hollow tubes. An apparatus of this general type is shown, for example, in U.S. Pat. No. 3,707,067 to Dietrick.

The Dietrick apparatus and similar designs have been found to be useful in applications such a gas scrubbing wherein the air drawn into the hollow tubes contains undesirable contaminants. The contaminated air is thoroughly intermixed with the liquid streams within the hollow tubes so that contaminants are removed from the air by the liquid before the air is discharged to atmosphere. The liquid is subsequently filtered by a device such as disclosed in U.S. Pat. No. 3,618,772.

One problem With apparatus of the type described above is that their usefulness is limited in applications wherein a relatively high vacuum is required, such as in high vacuum pumps or suction generators. In order to create a high vacuum within the suction chamber of such apparatus, air must be prevented from leaking from the outlet end of the hollow tubes into the suction chamber, i.e., in an upstream direction opposite to the flow of liquid and air therethrough. Although the liquid streams ejected from the nozzles into the hollow tubes tend to expand radially outwardly therein, no effective seal is created between the liquid stream and internal wall of the hollow tubes. As a result, a leakage path is provided for air to pass from the outlet end of the hollow tubes which is at approximately atmospheric pressure and the suction chamber which is at less than atmospheric pressure.

Another problem with apparatus of the type disclosed in U.S. Pat. No. 3,707,067 is that the manufacture and assembly thereof is made difficult by the large number of parts employed in their construction. For example, each of the nozzles and hollow tubes in such apparatus is a separate element mounted by a threaded connection within or in communication with the suction chamber. In addition, a number of structural elements are required to form the suction chamber and other parts of the apparatus. All of these elements must be interconnected by screws, and seals are employed therebetween to avoid fluid leakage. The many structural elements, seals and joint connections add expense and difficulty to the manufacture and assembly of apparatus such as disclosed in U.S. Pat. No. 3,707,067.

SUMMARY OF THE INVENTION

It is therefore among the objectives of this invention to provide a suction apparatus for use as a vacuum pump, suction generator, an aerator and the like which has a limited number of parts, which is easy to manufacture and assemble and which is capable of creating a relatively high vacuum.

These objectives are accomplished in an apparatus which comprises a fluid inlet housing, a cap, a base, and a pressure plate. All of these elements are formed in a one-piece, molded or extruded construction and are interconnected by circumferentially spaced bolts. The fluid inlet housing has an outer wall connected to a nozzle support plate formed with a plurality of circumferentially spaced nozzles. The outer wall of the fluid inlet housing rests atop a tube mounting plate in the base forming a suction chamber between the nozzle support plate o the fluid inlet housing and the mounting plate. This mounting plate of the base is integrally formed with a plurality of circumferentially spaced, hollow suction tubes each having an inlet oriented in direct alignment with the discharge outlet of a nozzle within the suction chamber. Stiffening ribs are formed on both the inner plate of the fluid inlet housing and mounting plate of the base to retain the nozzles and suction tubes in an axially aligned position. The top of the fluid inlet housing is closed by a cap having a tubular extension which is connected to a source of fluid, e.g., air, to be pumped and has an outlet within the suction chamber.

In operation, liquid under pressure is directed through the fluid inlet housing into each of the nozzles formed on the inner plate thereof. A liquid stream is ejected from the discharge outlet of each nozzle directly onto an aligning inlet of a hollow suction tube carried by the tube mounting plate of the base. In the course of passage from the nozzle into the suction tubes, the liquid streams create a negative pressure within the suction chamber which draws air or other fluid through the tubular extension of the cap, into the suction chamber and then into each of the suction tubes. The air intermixes with the liquid stream within each suction tube forming a combined air-water fluid stream which is discharged through the outlet of the suction tubes.

An important aspect of this invention is the provision of a means to ensure that a relatively high vacuum is created within the suction chamber. High vacuum is obtained in the instant invention by the provision of a pressure plate located in the path of the combined fluid streams ejected from the suction tubes of the base.

In the presently preferred embodiment, each of the suction tubes is formed with a passageway having a chamfered inlet end in alignment with the discharge outlet of a nozzle, a substantially cylindrical-shaped section extending longitudinally from the chamfered end and a radially outwardly flared section extending from the cylindrical section to the outlet end of the suction tube. In order to obtain a high vacuum within the suction chamber, a seal must be created at some point along the suction tube between the liquid ejected from the nozzles and the internal wall of the passageway formed in the suction tube. The pressure plate aids in creating this liquid seal.

It has been found that a back pressure is created when the combined fluid stream ejected from the outlet end of a suction tube contacts the pressure plate which radially outwardly expands or "fattens" the stream within the interior of the passageway in the suction tubes. Radial outward expansion of the stream creates an effective liquid seal at the internal wall of the passageway in the suction tubes which prevents the passage of air from the discharge or outlet end of the suction tubes, which are at slightly greater than atmospheric pressure, into the suction chamber which is at high negative pressure.

The pressure plate of this invention is positioned with respect to the outlet end of the suction tubes so as to produce a radially outward expansion of the liquid within the suction tubes without interfering with the free discharge of the combined fluid stream exiting the suction tubes. Depending upon the liquid pressure, the pressure plate is positioned in the range of about ⅜ of an inch to 1½ inches from the outlet ends of the suction tubes in order to operate effectively.

DESCRIPTION OF THE DRAWINGS

The structure, operation and advantages of the presently preferred embodiment of this invention will become further apparent upon consideration of the following description, taken in conjunction with the accompanying drawings, wherein:

FIG. 2 is a schematic cross sectional view of one nozzle, one suction tube and portion of the pressure plate illustrating the enlargement of the fluid stream within the interior of the suction tube to create an effective liquid seal therein; and FIG. 3 is a view similar to FIG. 2 except with the pressure plate removed to illustrate the formation of an air leakage path within the suction tube.

DETAILED DESCRIPTION OF THE INVENTION

Figure 1:
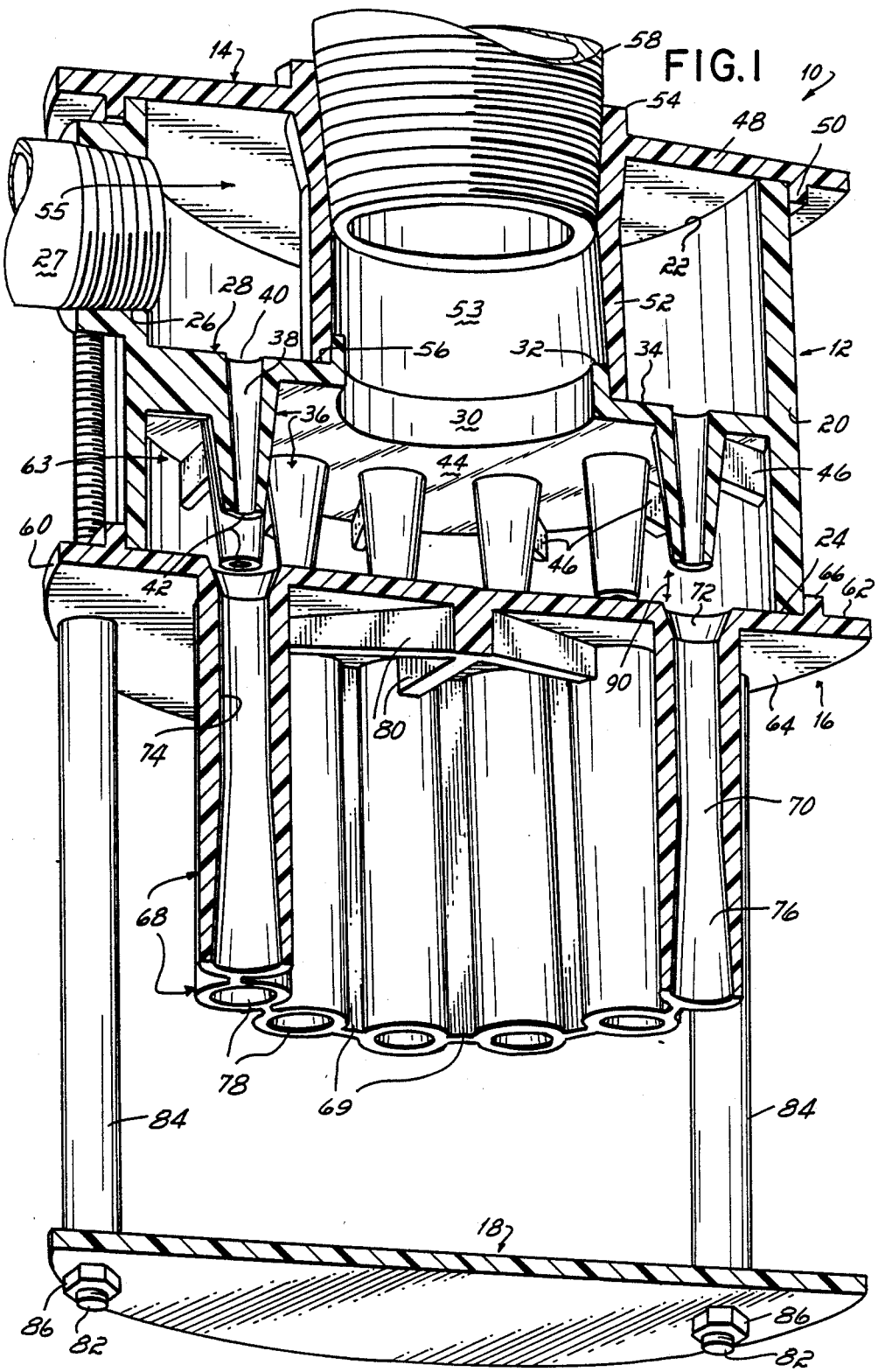
FIG. 1 is an enlarged, elevational view in partial cross section of the suction generator of this invention.

The apparatus 10 of this invention comprises a fluid inlet housing 12, a cap 14, a base 16 and a pressure plate 18 which are stacked vertically relative to one another and interconnected by bolts as described below. In the presently preferred embodiment, each of these structural elements of the apparatus 10 is formed from 30% glass-filled polypropylene in a molding or extrusion operation. As discussed below, the fluid inlet housing 12, cap 14, base 16 and pressure plate 18 are all formed in an integral, one-piece construction which greatly reduces the complexity and difficulty of manufacturing and assembling the apparatus 10.

The fluid inlet housing 12 is formed with an annular, outer wall 20 having an open top 22 and an open bottom 24. The outer wall 20 is formed with a threaded inlet passageway 26 which extends into the hollow interior of the fluid inlet housing 12. The inlet passageway 26 is adapted to connect to a pipe 27 carrying a liquid under pressure, as discussed below.

A nozzle support plate 28 is integrally formed within the interior of th fluid inlet housing 12 which extends radially inwardly from the outer wall 20 to a throughbore 30 formed in the center thereof. An annular lip 32 extends upwardly from the top surface 34 of support plate 28 concentric to the throughbore 30.

In the presently preferred embodiment, a plurality of nozzles 36 ar integrally formed in the nozzle support plate 28 at the same radius from the throughbore 30, and adjacent nozzles 36 are spaced equidistant from one another. Each nozzle 36 is formed with a passageway 38 having an inlet 40 at the top surface 34 of support plate 28 and a discharge outlet 42 on the opposite side of the nozzle support plate 28 spaced from its bottom surface 44. Preferably, the passageway 38 of each nozzle 36 tapers radially inwardly from the inlet 40 to the discharge outlet 42. In addition, a stiffening rib 46 is integrally formed on the bottom surface 44 of the nozzle support plate 28 between each of the nozzles 36 and the outer wall 20 of the fluid inlet housing 12. As discussed below, the purpose of these stiffening ribs 46 is to retain the discharge outlets 42 of the nozzles 36 in a fixed, axial position during operation of apparatus 10.

The cap 14 is formed to cover the open top 22 of the fluid inlet housing 12. The cap 14 comprises a top plate 48 having a bottom surface integrally formed with an annular lip 50 which, when the cap 14 is mounted to the fluid inlet housing 12, sealingly engages the exterior of the outer wall 20 of fluid inlet housing 12. The top plate 48 of cap 14 is integrally formed with a hollow, tubular extension 52, having an internal passageway 53, which is located within the interior of the fluid inlet housing 12. That portion of the tubular extension 52 within the interior of the fluid inlet housing 12 forms a liquid inlet cavity 55 which extends between the tubular extension 52 and the outer wall 20 of the fluid inlet housing 12.

The tubular extension 52 of cap 14 has a top end 54 which extends above the surface of top plate 48, and a bottom end 56 which rests atop the nozzle support plate 28 and sealingly engages the exterior surface of the annular lip 32 thereon. Preferably, at least the top portion of the internal wall of the tubular extension 52 is threaded to receive a pipe 58 connected to a source of fluid, such as air, to be pumped (not shown).

The base 16 comprises a suction tube support or mounting plate 60 having a top surface 62 and bottom surface 64. An annular lip 66 is integrally formed on the top surface 62 of tube mounting plate 60 which extends concentrically about the outer wall 20 of fluid inlet housing 12 with the apparatus 10 assembled. A space is formed between the nozzle support plate 28 of the fluid inlet housing 12 and the tube mounting plate 60 of base 16 defining a suction chamber 63 which communicates with th internal passageway 53 of the hollow tubular extension 52 of cap 14.

A plurality of suction tubes 68 are integrally formed on the tube support plate 60 at the same radial distance from the center thereof. Adjacent suction tubes 68 are interconnected by a wall section 69, and both the suction tubes 68 and wall sections 69 extend downwardly from the bottom surface 64 of tube mounting plate 60 as viewed in FIG. 1. Each suction tube 68 has a passageway 70 formed with a chamfered inlet 72 at the top surface 62 of tube mounting plate 60, a cylindrical-shaped upper section 74 extending downwardly from the chamfered inlet 72 and a radially outwardly tapered discharge section 76 extending from the upper section 74 to the outlet end 78 of the suction tube 68. The chamfered inlet 72 of each suction tube 68 axially aligns with and is spaced from the discharge outlet 42 of one of the nozzles 36. At least every other suction tube 68 is connected to a stiffening rib 80 which is formed on the bottom surface 64 of the tube mounting plate 60 and extends radially outwardly from the center of such mounting plate 60 to the suction tube 68. These stiffening ribs 80 help maintain the suction tubes 68 in a fixed axial position relative to the nozzles 36 for purposes to become apparent below.

The pressure plate 18 is located directly in alignment with the discharge outlets 78 of the suction tubes 68, preferably at a distance in the range of about ¾ inch to 1½ inches therefrom to avoid a restriction of the fluid flow. The pressure plate 18 is mounted in this position with respect to the suction tubes 68 by lag screws 82 which extend from the top plate 48 of cap 14, through the tube support plate 60 of base 16 and then through a sleeve 84 located between the tube support plate 60 and pressure plate 18. As shown at the bottom of FIG. 1, the lag screws 82 are secured in place by nuts 86. Additional lag screw (not shown) are connected between the top plate 48 of cap 14 and tube support plate 60 to maintain the apparatus 10 in assembled relation.

The apparatus 10 operates as follows. A liquid such as water is pumped under pressure through the pipe 27 into the inlet passageway 26 in the fluid inlet housing 12 to the liquid inlet cavity 55 formed between the tubular extension 52 of cap 14 and the outer wall 20 of fluid inlet housing 12. The pressurized liquid flows from the liquid inlet cavity 55 into the inlets 40 of the nozzle 36 and is accelerated through the passageway 38 in each nozzle 36 to its discharge outlet 42 located within the suction chamber 63. An air gap or space 90 is formed within the suction chamber 63 between the discharge outlet 42 of each nozzle 36 and an aligning chamfered inlet 72 of each suction tube 68 formed in the tube mounting plate 60 of base 16. A liquid stream 92 is ejected from the discharge outlet 42 of each nozzle 36, through this space 90 and into the chamfered inlet 72 of each suction tube 68. In the course of passage from the nozzles 36 into the suction tubes 68, these liquid streams 92 create a negative pressure within the suction chamber 63 and within the internal passageway 53 of the hollow, tubular extension 52 of cap 14.

As shown in FIG. 2, the liquid stream 92 expands radially outwardly upon entering the suction tube 68, but a gap 96 is formed along at least a portion of the upper section 74 of the passageway 70 within suction tube 68 and the periphery of the liquid stream 92. Air or other fluid introduced into the suction cavity 63 through the tubular extension 52 of cap 14 is drawn into this gap 96 and intermixes with the liquid stream 92 therein. A combined liquid-air or fluid stream 98 is thus formed within suction tube 68 which continues to expand radially outwardly in the course of passage through the tapered discharge section 76 of passageway 70.

The fluid stream 98 is ejected from the discharge outlet 78 of each suction tube 68 and impacts against the pressure plate 18 aligned therewith. Contact between the rapidly moving fluid stream 98 and the pressure plate 18 creates a back pressure in an upstream direction, i.e., toward the discharge outlets 78 of suction tubes 68. As a result of this back pressure, the fluid stream 98 is forced to radially outwardly expand or enlarge within the suction tube 68 forming a liquid seal against the wall of passageway 70 at location along either the cylindrical-shaped upper section 74 or tapered discharge section 76 thereof. This liquid seal prevents air from leaking upstream along the passageway 70 from its discharge outlet 78 toward its chamfered inlet 72 which would otherwise reduce the negative pressure created in the suction chamber 63.

In the absence of the pressure plate 18, as shown in FIG. 3, the fluid stream 98 can pass through the suction tubes 68 without sealing against the wall thereof. As a result, a continuous gap 100 is formed between the stream 98 and suction tube wall along which air can flow upstream from the discharge outlet 78 of suction tube 68 into the suction chamber 63.

The embodiment of this invention illustrated in FIG. 3 is acceptable for use in applications which require relatively low negative pressure. The embodiment of FIGS. 1 and 2 is used for higher negative pressure applications, and the vacuum or negative pressure obtained is a function of the pressure and flow rate of the fluid, e.g., water, pumped into the fluid inlet housing 12. For example, at a water pressure of 10 pounds per square inch (p.s.i.) and a flow rate of 29 gallons per minute (g.p.m.), a negative pressure of about 5 inches mercury (in. Hg.) is obtained within the suction chamber 63 of the apparatus 10 illustrated in FIGS. 1 and 2. The negative pressure within suction chamber 63 can be increased to about 27 in. Hg. by increasing the water pressure to 54 p.s.i. and the flow rate to 66.5 g.p.m. Intermediate levels of vacuum within suction chamber 63 between 5 and 27 in. Hg. are obtained by varying the pressure and flow rate of the water entering housing 12 from 10 p.s.i. and 29 g.p.m. to 54 p.s.i. and 66.5 g.p.m.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. Apparatus for pumping a fluid, comprising:
   a suction chamber adapted to communicate with a source of a first fluid to be pumped;
   first means having a passageway formed with an inlet and an outlet, said inlet communicating with said suction chamber;
   second means for ejecting a stream of a second fluid through said suction chamber and into said passageway of said first means, said stream of a second fluid being effective to create a negative pressure within said suction chamber in the course of passage between said second means and said passageway of said first means which draws s id first fluid into said passageway for combination with said second fluid to form a combined fluid stream within said passageway, said combined fluid stream being ejected in a first direction from said outlet of said passageway;
   deflection means located in the path of said combined fluid stream ejected from said outlet of said passageway for deflecting said combined fluid stream and creating a back pressure which is effective to expand said combined fluid stream within said passageway of said first means to create a fluid seal therein and substantially prevent the flow of air in said second direction through said passageway and into said suction chamber.

2. The apparatus of claim 1 in which said deflection means comprises a pressure plate spaced from said discharge outlet of said suction tube.

3. The apparatus of claim in which said pressure plate is spaced in the range of about three-quarters of an inch to one and one-half inch from said discharge outlet of each of said suction tubes.

4. Apparatus for pumping a fluid, comprising:
a suction chamber communicating with a source of a first fluid to be pumped;
at least one nozzle formed with an inlet and a discharge outlet, said discharge outlet being located within said suction chamber;
at least one suction tube formed with a passageway having an inlet and an outlet, said inlet being aligned with and spaced from said discharge outlet of said nozzle, an air gap being formed between said discharge outlet of said nozzle and said inlet of said suction tube within said suction chamber;
means for directing a second fluid into said nozzle, said nozzle being effective to eject said second fluid from said discharge outlet, through said air gap within said suction chamber and into said inlet of said passageway in said suction tube, said second fluid creating a negative pressure within said suction chamber in the course of passage through said air gap which draws said first fluid from said suction chamber into said passageway of said suction tube, said first and second fluids intermixing within said passageway to form a combined fluid stream which is ejected in a first direction from said outlet of said suction tube;
deflection means located in the path of said combined fluid stream ejected from said outlet of said suction tube for deflecting said combined fluid stream and creating a back pressure which is effective to expand said combined fluid stream within said passageway of said suction tube to create a fluid seal within said passageway and substantially prevent the flow of air in said second direction through said passageway and into said suction cavity.

5. The apparatus of claim 4 in which said deflection means comprises a pressure plate spaced from said outlet of said suction tube.

6. The apparatus of claim 5 in which said pressure plate is spaced in the range of about three-quarters of an inch to one and one-half inch from said outlet of each of said suction tubes.

7. Apparatus for pumping a fluid, comprising:
a fluid inlet housing including an outer wall formed with first and second ends, said outer wall having an inlet adapted to connect to a source of liquid under pressure;
a nozzle support plate mounted to said outer wall within said interior of said fluid inlet housing, said nozzle support plate supporting a plurality of nozzles each having an inlet on one side of said nozzle support plate and a discharge outlet on the opposite side of said nozzle support plate;
a base having a tube mounting plate which supports said second end of said outer wall of said fluid inlet housing, said tube mounting plate being spaced from said nozzle support plate of said fluid inlet housing forming a suction chamber therebetween, said tube mounting plate supporting plurality of suction tubes each having a passageway formed with an inlet aligned with and spaced from said discharge outlet of one of said nozzles within said suction chamber, and an outlet located outside of said suction chamber;
a cap mounted to said first end of said outer wall of said fluid inlet housing, said cap being formed with a tubular extension located within said interior of said fluid inlet housing which communicates with said suction chamber, said tubular extension being adapted to communicate with a source of a gas to be pumped;
said fluid inlet housing receiving liquid under pressure through said inlet in said outer wall which flows into said nozzles, each of said nozzles being effective to eject a liquid stream from said discharge outlet thereof into said inlet of said suction tubes, said liquid streams being effective to create a negative pressure within said suction chamber in the course of passage from said nozzle into said suction tubes which draws said gas to be pumped from said tubular extension, through said suction chamber and into said passageway of said suction tubes, said gas intermixing with said liquid stream within said passageway of said suction tubes to form a combined fluid stream which is ejected from said outlet of said suction tubes;
a deflector plate located in the path of said combined fluid stream ejected from said outlet of said suction tubes, said deflector plate being effective to deflect said combined fluid stream and create a back pressure within said outlet of said suction tubes so that said combined fluid stream within said passageway in said suction tubes expands and forms a fluid seal within said passageway to substantially prevent the flow of air from said outlet of said suction tubes and into said suction chamber.

8. The apparatus of claim 7 including stiffening means for maintaining said nozzles in an axially aligned position with respect to said suction tubes in said base.

9. The apparatus of claim 8 in which said stiffening means comprises a plurality of ribs integrally formed on said nozzle support plate of said fluid inlet housing, each of said ribs extending between said cylindrical-shaped wall thereof and one of said nozzles.

10. The apparatus of claim 7 including stiffening means integrally formed on said tube mounting plate of said base for maintaining said suction tubes in an axially aligned position with respect to said nozzles of said fluid inlet housing.

11. The apparatus of claim 10 in which said stiffening means comprises a plurality of ribs each extending radially outwardly from the center of said tube mounting plate of said base to one of said suction tubes.

12. Apparatus for pumping a fluid, comprising:
a one-piece, integrally formed fluid inlet housing, including:
  (i) a cylindrical-shaped wall defining a hollow interior, said wall being formed with first and second ends and an inlet adapted to connect to a source of a first fluid;
  (ii) an annular, nozzle support plate integrally formed within said hollow interior and extending radially inwardly from said wall, said nozzle support plate having a central passageway and a plurality of throughbores radially spaced from said central passageway;
  (iii) a plurality of nozzles integrally formed on said nozzle support plate, each of said nozzles having an inlet at one of said throughbores in said nozzle support plate and a discharge outlet;
a one-piece cap integrally formed with a tubular extension adapted to connect to a source of a second fluid to be pumped, said cap being mounted to said first end of said cylindrical-shaped wall of said fluid inlet housing so that said tubular extension seats against said nozzle support plate over said central passageway therein, a fluid inlet chamber being formed within said hollow interior of said fluid inlet housing between said cylindrical-shaped wall and said tubular extension;

a one-piece base including
  (i) an annular tube mounting plate having a plurality of throughbores radially spaced from the center thereof, said tube mounting plate supporting said second end of said cylindrical-shaped wall of said fluid inlet housing forming a suction chamber between said tube mounting plate and said nozzle mounting plate of said fluid inlet housing; and
  (ii) a plurality of suction tubes integrally formed on said tube mounting plate, each of said suction tubes having a passageway formed with an inlet at one of said throughbores in said tube mounting plate within said suction cavity in alignment with a discharge outlet of one of said nozzles, and an outlet outside of said suction chamber;

said first fluid being introduced under pressure into said fluid inlet chamber of said fluid inlet housing and then to said nozzles, said nozzles being effective to eject a stream of said first fluid into said passageway of said suction tubes in said base thereby creating a negative pressure within said suction chamber and within said tubular extension of said cap to draw the second fluid into said tubular extension, through said suction chamber and into said suction tubes, said first and second fluid being combined within said suction tubes to form a combined fluid stream which is ejected in a first direction from said outlet of said deflector means located in the path of said combined fluid stream ejected from said outlet of said suction tubes for deflecting said combined fluid stream and creating a back pressure which is effective to expand said combined fluid stream within said passageway of each said suction tubes to create a fluid seal within said passageways and substantially prevent the flow of air in a second direction opposite said first direction through said passageways and into said suction cavity.

13. The apparatus of claim 12 including stiffening means for maintaining said nozzles in an axially aligned position with respect to said suction tubes in said base.

14. The apparatus of claim 13 in which said stiffening means comprises a plurality of ribs integrally formed on said nozzle support plate of said fluid inlet housing, each of said ribs extending between said cylindrical-shaped wall thereof and one of said nozzles.

15. The apparatus of claim 12 including stiffening means integrally formed on said tube mounting plate of said base for maintaining said suction tube in an axially aligned position with respect to said nozzles of said fluid inlet housing.

16. The apparatus of claim 15 in which said stiffening means comprises a plurality of ribs each extending radially outwardly from the center of said tube mounting plate of said base to one of said suction tubes.

17. The method of pumping a fluid, comprising:
ejecting a first fluid stream from the discharge outlet of a nozzle located within a suction chamber into the inlet of a passageway which is spaced from said discharge outlet of said nozzle;

creating a negative pressure within said suction chamber in the course of passage of said first fluid stream between said nozzle and said passageway to draw a second fluid through said suction chamber and into said passageway for combination with said first fluid to form a combined fluid stream within said passageway;

discharging said combined fluid stream from the outlet of said passageway in a first direction;

impacting said combined fluid stream discharged from said outlet in said passageway against a surface located in the path of said combined fluid stream to create a back pressure which causes said combined fluid stream to radially outwardly expand and form a fluid seal within said passageway to substantially prevent the passage of air from said outlet of said passageway into said suction chamber.

* * * * *

UNITED STATES PATENT AND TRADEMARK OFFICE
CERTIFICATE OF CORRECTION

PATENT NO. : 4,932,842

DATED : June 12, 1990

INVENTOR(S) : Gerald P. Dietrick and Michael J. Vagedes

It is certified that error appears in the above-identified patent and that said Letters Patent is hereby corrected as shown below:

In column 1, line 30, "a" should be --as--.

In column 1, line 38, "With" should be --with--.

In column 2, line 21, "o" should be --of--.

In column 3, line 15, "3/4of" should be --3/4 of--.

In column 3, line 58, "th" should be --the--.

In column 3, line 64, "ar" should be --are--.

In column 4, line 42, "th" should be --the--.

In column 5, line 2, "1 1/2inches" should be --1-1/2 inches--.

In column 6, line 49, "s id" should be --said--.

In column 6, line 67, "of claim in" should be --of claim 1 in--.

UNITED STATES PATENT AND TRADEMARK OFFICE
CERTIFICATE OF CORRECTION

PATENT NO. : 4,932,842

DATED : June 12, 1990

INVENTOR(S) : Gerald P. Dietrick and Michael J. Vagedes

It is certified that error appears in the above-identified patent and that said Letters Patent is hereby corrected as shown below:

In column 7, line 60, after "supporting", insert --a--.

In column 9, line 35, after "outlet of said", insert --suction tubes;--, and then continue with a new paragraph for the remainder of the claim.

In column 10, line 13, "tube" should be --tubes--.

Signed and Sealed this

Twelfth Day of November, 1991

Attest:

HARRY F. MANBECK, JR.

*Attesting Officer*　　　　　　　　*Commissioner of Patents and Trademarks*